(12) United States Patent
Ramsay et al.

(10) Patent No.: US 10,675,061 B2
(45) Date of Patent: Jun. 9, 2020

(54) POLYAXIAL BONE FIXATION ELEMENT

(71) Applicant: Medos International Sarl, Le Locle (CH)

(72) Inventors: Christopher Ramsay, West Wareham, MA (US); John DiVincenzo, Braintree, MA (US)

( * ) Notice: Subject to any disclaimer, the term of this patent is extended or adjusted under 35 U.S.C. 154(b) by 346 days.

(21) Appl. No.: 15/441,326

(22) Filed: Feb. 24, 2017

(65) Prior Publication Data
US 2017/0245894 A1   Aug. 31, 2017

Related U.S. Application Data

(60) Provisional application No. 62/300,456, filed on Feb. 26, 2016.

(51) Int. Cl.
*A61B 17/70*  (2006.01)
*A61B 17/86*  (2006.01)

(52) U.S. Cl.
CPC ...... *A61B 17/7001* (2013.01); *A61B 17/7037* (2013.01); *A61B 17/7038* (2013.01); *A61B 17/8605* (2013.01); *A61B 17/8685* (2013.01)

(58) Field of Classification Search
CPC ............ A61B 17/7032; A61B 17/7034; A61B 17/7035; A61B 17/7037; A61B 17/7038; A61B 17/861; A61B 17/862; A61B 2017/8655
See application file for complete search history.

(56) References Cited

U.S. PATENT DOCUMENTS

| | | |
|---|---|---|
| 4,946,458 A | 8/1990 | Biedermann |
| 5,443,467 A | 8/1995 | Biedermann et al. |
| 5,536,268 A | 7/1996 | Griss |
| 5,672,176 A | 9/1997 | Biedermann et al. |
| 5,733,285 A | 3/1998 | Errico et al. |
| 5,733,286 A | 3/1998 | Errico et al. |
| 5,782,833 A | 7/1998 | Haider |
| 5,879,350 A | 3/1999 | Sherman et al. |
| 5,885,286 A | 3/1999 | Sherman et al. |
| 5,891,145 A | 4/1999 | Morrison et al. |
| 5,961,517 A | 10/1999 | Biedermann et al. |
| 6,063,090 A | 5/2000 | Schlapfer |

(Continued)

FOREIGN PATENT DOCUMENTS

| | | |
|---|---|---|
| CN | 103565504 A | 2/2014 |
| DE | 10005386 A1 | 8/2001 |

(Continued)

*Primary Examiner* — Anu Ramana
(74) *Attorney, Agent, or Firm* — BakerHostetler

(57) ABSTRACT

A fastener device includes an anchor body that defines a through hole. The anchor body further includes an inner surface that defines a least a portion of the through hole. The fastener includes a head, a threaded shaft that extends out with respect to the head in a distal direction, and a neck between the head and threaded shaft. The head includes an outer surface configured to articulate along the inner surface when the fastener head is inserted in the through hole. At least a portion of the outer surface is convex and defines a portion of a sphere that defines a first diameter. The neck defines a second diameter and the fastener defines a ratio of the first diameter to the second diameter in a range between about 2 to 1 and about 3 to 1.

28 Claims, 12 Drawing Sheets

(56) References Cited

U.S. PATENT DOCUMENTS

| | | |
|---|---|---|
| 6,090,111 A | 7/2000 | Nichols |
| 6,113,601 A | 9/2000 | Tatar |
| 6,248,105 B1 | 6/2001 | Schlapfer et al. |
| 6,254,602 B1 | 7/2001 | Justis |
| 6,280,442 B1 | 8/2001 | Barker et al. |
| 6,287,311 B1 | 9/2001 | Sherman et al. |
| 6,355,040 B1 | 3/2002 | Richelsoph et al. |
| 6,371,957 B1 | 4/2002 | Amrein et al. |
| 6,402,752 B2 | 6/2002 | Schaffler-Wachter et al. |
| 6,471,705 B1 | 10/2002 | Biedermann et al. |
| 6,485,491 B1 | 11/2002 | Farris et al. |
| 6,540,748 B2 | 4/2003 | Lombardo |
| 6,554,834 B1 * | 4/2003 | Crozet ............... A61B 17/7037 606/272 |
| 6,582,436 B2 | 6/2003 | Schlapfer et al. |
| 6,585,737 B1 | 7/2003 | Baccelli et al. |
| 6,660,004 B2 | 12/2003 | Barker et al. |
| 6,835,196 B2 | 12/2004 | Biedermann et al. |
| 6,837,889 B2 | 1/2005 | Shluzas |
| 6,869,433 B2 | 3/2005 | Glascott |
| 7,066,937 B2 | 6/2006 | Shluzas |
| 7,087,057 B2 | 8/2006 | Konieczynski et al. |
| 7,144,396 B2 | 12/2006 | Shluzas |
| 7,563,264 B2 * | 7/2009 | Landry ............... A61B 17/1604 606/86 A |
| 7,604,656 B2 | 10/2009 | Shluzas |
| 7,682,377 B2 | 3/2010 | Konieczynski et al. |
| 7,699,876 B2 | 4/2010 | Barry et al. |
| 7,727,261 B2 | 6/2010 | Barker et al. |
| 7,879,075 B2 | 2/2011 | Shluzas |
| 7,942,910 B2 | 5/2011 | Doubler et al. |
| 7,951,173 B2 | 5/2011 | Hammill, Sr. et al. |
| 8,021,397 B2 | 9/2011 | Farris et al. |
| 8,062,339 B2 | 11/2011 | Hammer et al. |
| 8,167,914 B1 | 5/2012 | Hunt et al. |
| 8,197,517 B1 | 6/2012 | Lab et al. |
| 8,298,274 B2 | 10/2012 | Barker, Jr. et al. |
| 8,313,516 B2 | 11/2012 | Konieczynski et al. |
| 8,337,530 B2 | 12/2012 | Hestad et al. |
| 8,444,681 B2 | 5/2013 | Surber |
| 8,529,604 B2 | 9/2013 | Barker, Jr. et al. |
| 8,556,938 B2 | 10/2013 | Surber |
| 8,663,288 B2 | 3/2014 | Konieczynski et al. |
| 8,663,290 B2 | 3/2014 | Doubler et al. |
| 8,709,050 B2 | 4/2014 | Shluzas |
| 8,709,051 B2 | 4/2014 | Hammer et al. |
| 8,814,919 B2 * | 8/2014 | Barrus ............... A61B 17/7037 606/266 |
| 8,906,068 B1 | 12/2014 | Bedor |
| 8,936,624 B2 | 1/2015 | Shluzas |
| 8,951,290 B2 | 2/2015 | Hammer et al. |
| 8,998,959 B2 | 4/2015 | Surber |
| 9,023,086 B2 | 5/2015 | Biedermann et al. |
| 9,149,300 B2 | 10/2015 | Biedermann et al. |
| 9,168,069 B2 | 10/2015 | Surber |
| 9,186,191 B2 | 11/2015 | Berrevoets et al. |
| 9,232,969 B2 | 1/2016 | Farris |
| 9,241,737 B2 | 1/2016 | Biedermann et al. |
| 9,271,761 B2 | 3/2016 | Legallois et al. |
| 2003/0176861 A1 | 9/2003 | Reed |
| 2004/0267264 A1 | 12/2004 | Konieczynski et al. |
| 2006/0235385 A1 | 10/2006 | Whipple |
| 2011/0087288 A1 | 4/2011 | Stevenson et al. |
| 2012/0089150 A1 | 4/2012 | Smith |
| 2012/0136395 A1 | 5/2012 | Hagle |
| 2012/0143265 A1 | 6/2012 | Pohl |
| 2012/0165881 A1 | 6/2012 | Meer |
| 2012/0253408 A1 | 10/2012 | Timm |
| 2012/0303072 A1 | 11/2012 | Eisermann |
| 2012/0310284 A1 | 12/2012 | Gerchow |
| 2013/0066376 A1 | 3/2013 | Biedermann et al. |
| 2013/0096620 A1 | 4/2013 | Meer |
| 2013/0165977 A1 | 6/2013 | Biedermann et al. |
| 2013/0197586 A1 | 8/2013 | Matthis et al. |
| 2013/0338716 A1 | 12/2013 | Biedermann et al. |
| 2014/0012337 A1 | 1/2014 | Biedermann et al. |
| 2014/0121703 A1 | 5/2014 | Surber |
| 2014/0163618 A1 | 6/2014 | Legallois et al. |
| 2014/0188173 A1 | 7/2014 | Perkins |
| 2014/0343617 A1 | 11/2014 | Hannen |
| 2014/0358182 A1 | 12/2014 | Puekert |
| 2015/0032162 A1 | 1/2015 | Biedermann et al. |
| 2015/0282844 A1 | 10/2015 | Vedula et al. |
| 2016/0000470 A1 | 1/2016 | Matthis et al. |
| 2016/0030086 A1 | 2/2016 | Mishra |
| 2016/0038204 A1 | 2/2016 | Matthis |
| 2016/0045228 A1 | 2/2016 | Biedermann et al. |

FOREIGN PATENT DOCUMENTS

| | | |
|---|---|---|
| EP | 1210914 A1 | 6/2002 |
| EP | 2687171 A1 | 1/2014 |
| EP | 2687172 A1 | 1/2014 |
| EP | 2740424 A1 | 6/2014 |
| WO | 00/76413 A1 | 12/2000 |
| WO | 01/06940 A1 | 2/2001 |
| WO | 01/10317 A1 | 2/2001 |
| WO | 2003/037199 A1 | 5/2003 |
| WO | 2012/088890 A1 | 7/2012 |
| WO | 2016/020158 A1 | 2/2016 |

* cited by examiner

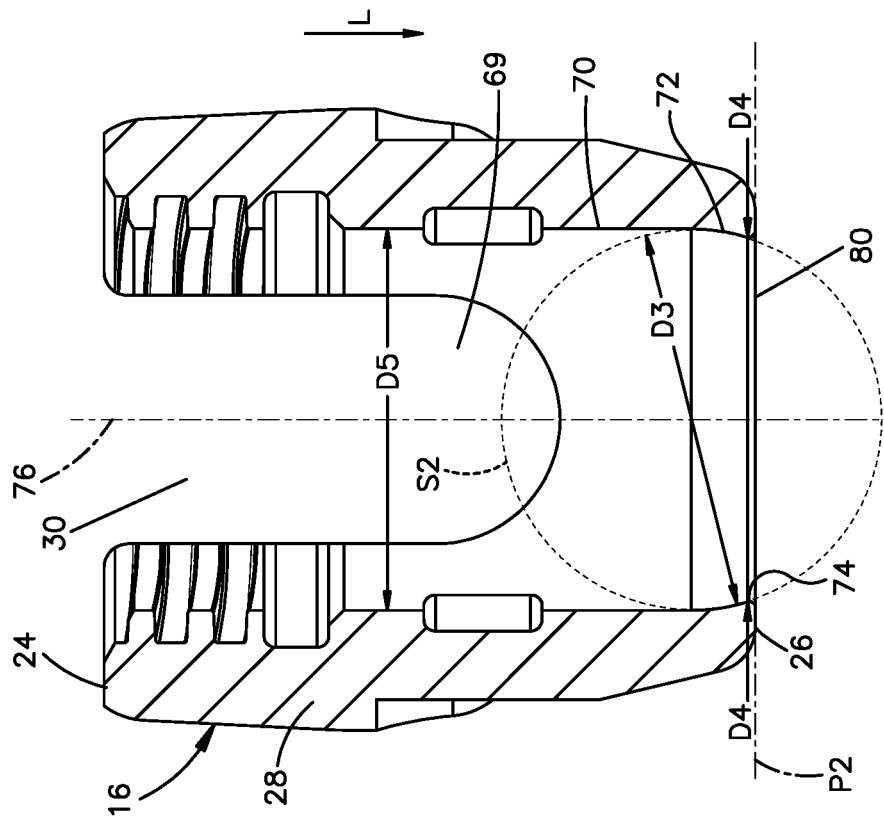
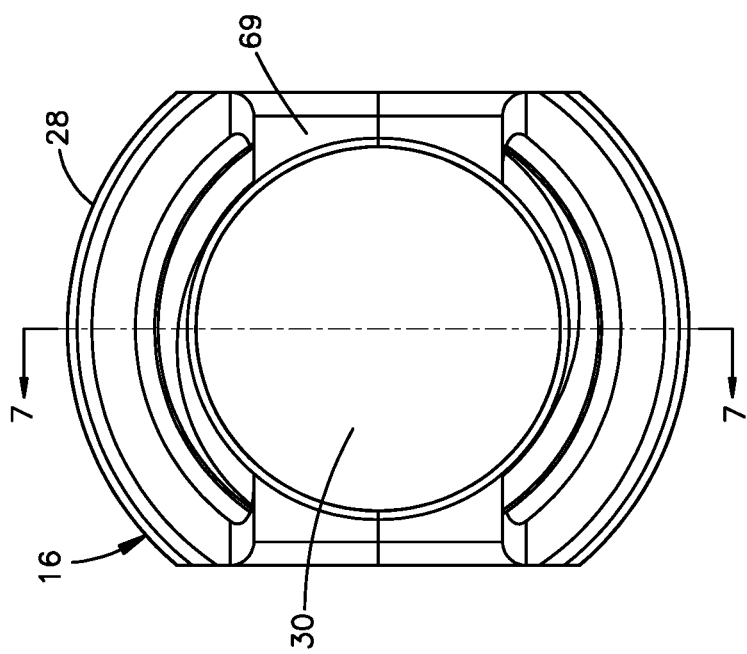

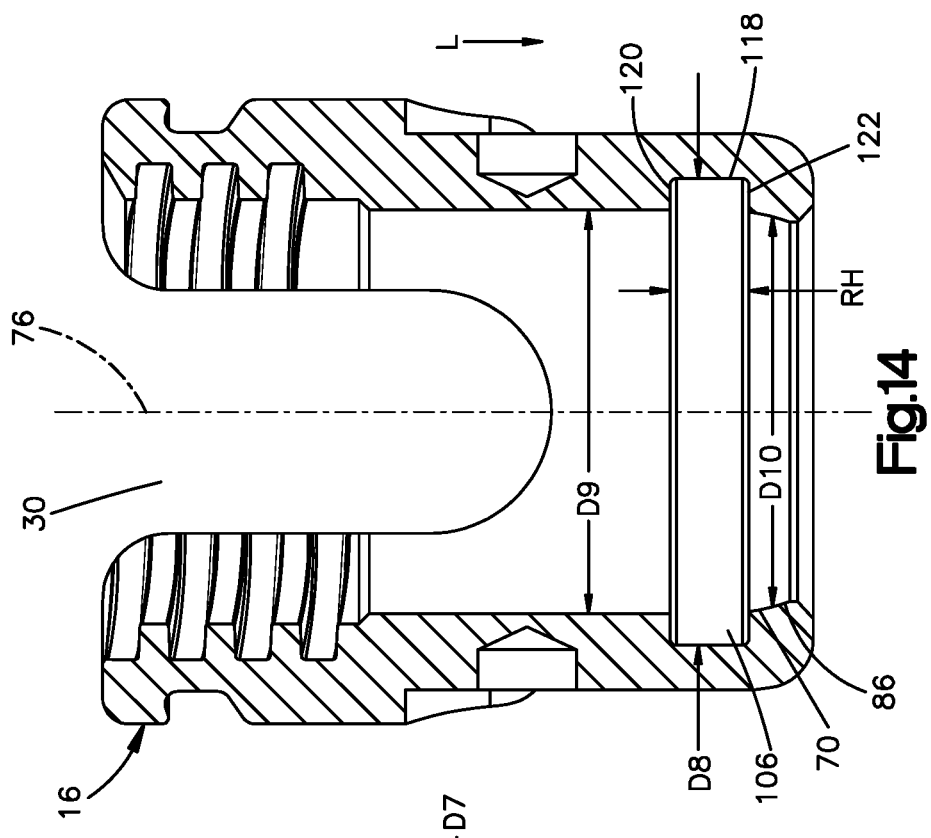
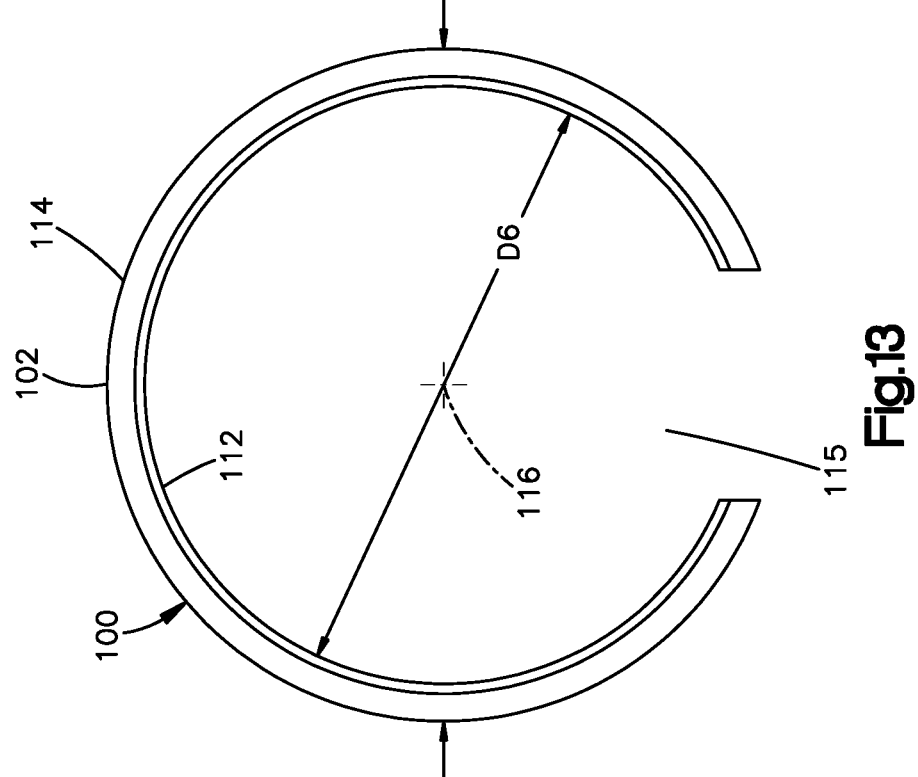

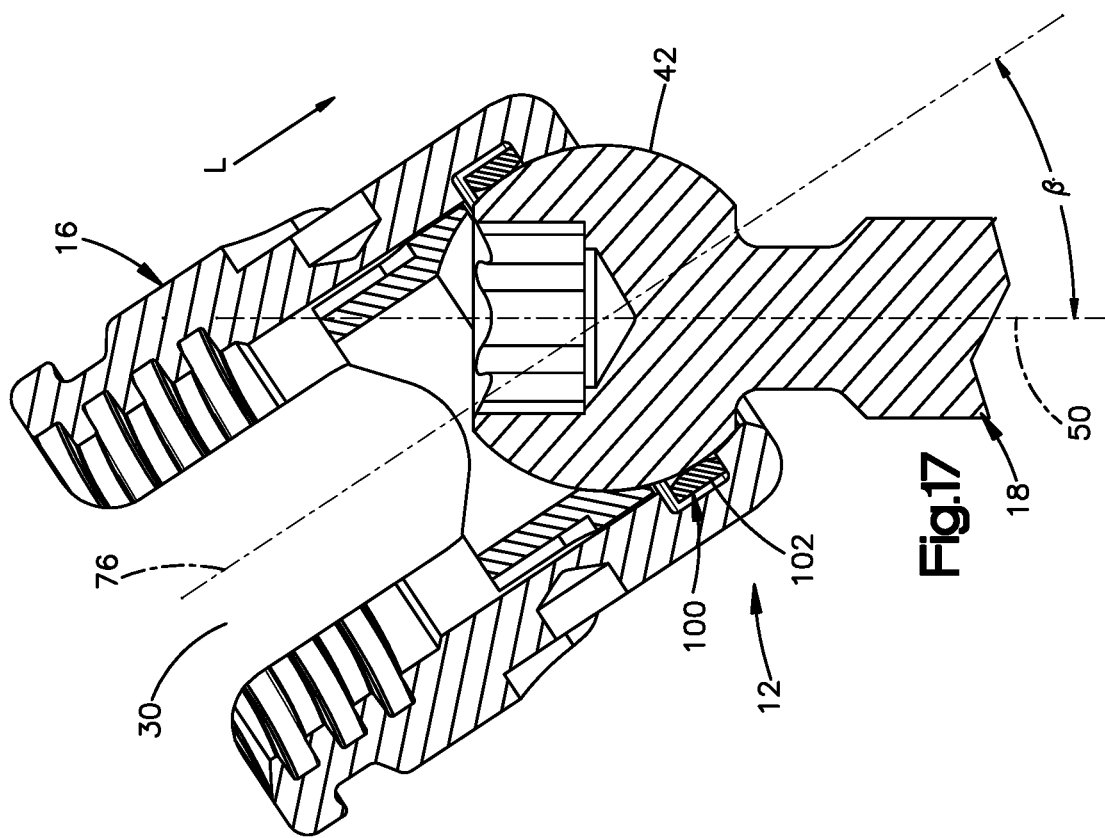
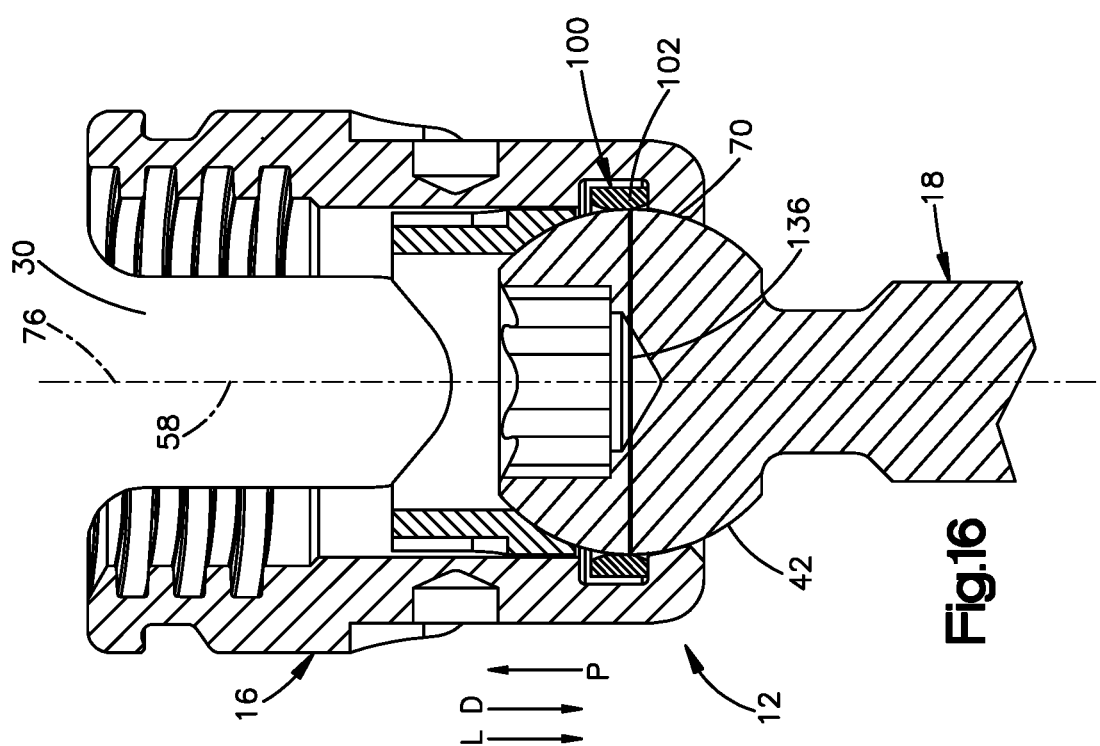

POLYAXIAL BONE FIXATION ELEMENT

CROSS REFERENCE TO RELATED APPLICATIONS

This application claims the benefit of U.S. Provisional Application No. 62/300,456, filed Feb. 26, 2016, the contents of which are hereby incorporated by reference as if set forth in their entirety herein.

TECHNICAL FIELD

The present application relates generally to medical devices. More specifically, the present application is related to devices, kits, and methods for treatment of a spine.

BACKGROUND

Various spinal disorders may be surgically corrected to stabilize a patient's spinal column. Spinal disorders may include curvatures or other defects that are correctable with a spinal fusion procedure. One method of spinal fusion involves one or more elongated members, typically spinal rods, longitudinally placed on the posterior spine. When a pair of elongated members is used in the spinal fusion procedure, the elongated members may be placed on either side of spinous processes of the vertebral column, for example.

Each elongated member may be attached to one or more of the vertebrae of the spine by way of fastener devices. The fastener devices each may include an anchor body defining a rod-receiving channel configured to receive a portion of the elongated member therein, and a locking cap configured to clamp and secure the position of the elongated member within the rod-receiving channel. The fastener devices each may further include a fastener configured to secure the anchor body to a vertebra.

To facilitate insertion of the elongated members into the rod-receiving channels and to provide additional flexibility in the positioning of the elongated members and the fastener devices, fastener devices have been developed wherein the anchor body is pivotable with respect to the fastener. These fastener devices may be referred to as polyaxial fastener devices.

It is desirable to develop a fastener device that is simple for a surgeon to use, that provides for polyaxial rotation and is able to securely mount the elongated member to a patient's spine.

SUMMARY

In accordance with an aspect of the disclosure, the present application discloses a fastener device comprising an anchor body and a fastener. The anchor body including an anchor body housing, the anchor body defining a through hole that extends through the anchor body housing, the anchor body further including an upper end, a lower end, and an inner surface, and the inner surface defining a least a portion of the through hole. The fastener including a head, a threaded shaft that extends out with respect to the head in a distal direction, and a neck that extends between the head and the threaded shaft. The head including an outer surface configured to articulate along the inner surface when the fastener head is inserted in the through hole, at least a portion of the outer surface being convex and defining a portion of a sphere, the sphere defining a first outer diameter, and the fastener including a concave surface that extends along both the head and the neck, the neck defining a second outer diameter measured: 1) in a direction perpendicular to the distal direction, and 2) at a location spaced in the distal direction of an entirety of the concave surface, wherein the screw defines a ratio of the first outer diameter to the second outer diameter in a range between about 2 to 1 and about 3 to 1.

In accordance with an aspect of the disclosure, the present application discloses a fastener device comprising an anchor body and a fastener. The anchor body including an anchor body housing, the anchor body defining a through hole that extends through the anchor body housing, the anchor body further including an upper end, a lower end, and an inner surface that defines a least a portion of the through hole, and at least a portion of the inner surface defining a portion of a first sphere. The fastener including a head, a threaded shaft that extends out with respect to the head in a distal direction, and a neck that extends between the head and the threaded shaft. The head including an outer surface, at least a portion of the outer surface defining a portion of a second sphere, and the head further including a concave surface of the fastener that extends along both the head and the neck. The fastener device defines a configuration in which both: 1) the portion of the outer surface rides along the portion of the inner surface, and 2) the anchor body abuts the neck at a location that is spaced in the distal direction from an entirety of the concave surface such that movement of the fastener relative to the anchor body in at least one direction is blocked.

In accordance with an aspect of the disclosure, the present application discloses a fastener device comprising an anchor body and a fastener. The anchor body including an anchor body housing, the anchor body defining a through hole that extends through the anchor body housing, the anchor body further including an upper end, a lower end, and an inner surface, and the inner surface defining at least a portion of the through hole. The fastener including a head, a threaded shaft that extends out with respect to the head in a distal direction, and a neck that extends between the head and the threaded shaft. The head including a convex outer surface, a portion of the convex surface both defining a portion of a sphere and being configured to articulate along the inner surface when the fastener head is positioned in the through hole, and the fastener including a concave surface that extends along both the head and the neck. Wherein the fastener is configured such that all lines that: 1) lie entirely within a plane parallel to the distal direction, and 2) are tangent to the portion of the convex outer surface are noncollinear with all lines that: 1) lie entirely within the plane, and 2) are tangent to the concave surface.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

FIG. 6 is a top plan view of an anchor body of the fastener device illustrated in FIG. 1;

FIG. 7 is a cross-sectional view of the anchor body illustrated in FIG. 6, along line 7-7;

FIG. 13 is a top plan view of the biasing member illustrated in FIG. 12;

FIG. 14 is a cross-sectional view of the anchor body illustrated in FIG. 12, along line 14-14;

FIG. 16 is a cross-sectional view of the fastener device illustrated in FIG. 12, along line 14-14, the fastener device in a first configuration; and FIG. 17 is a cross-sectional view of the fastener device illustrated in FIG. 12, along line 14-14, the fastener device in a second configuration.

DETAILED DESCRIPTION

Figure 1:
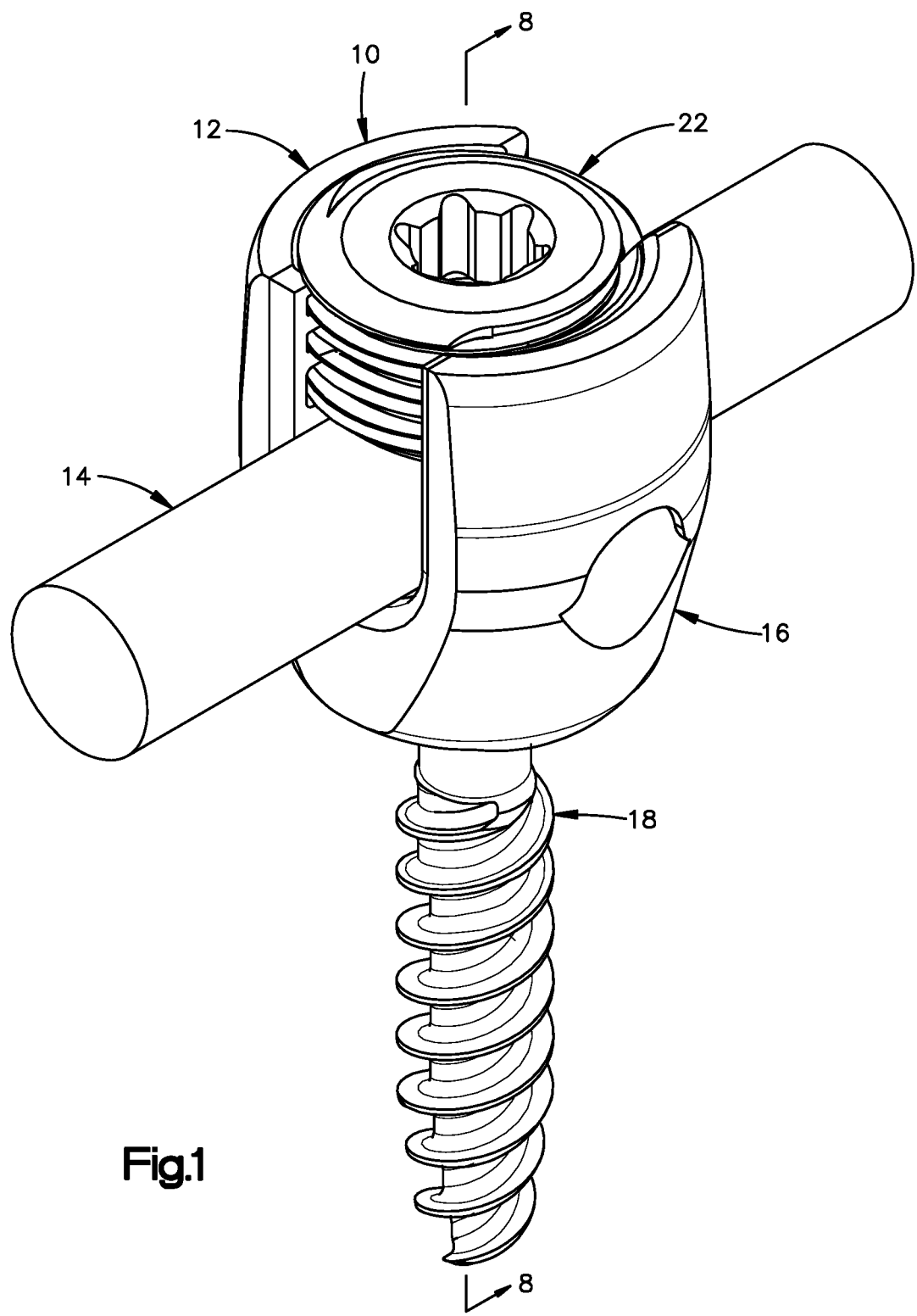
FIG. 1 is an isometric view of a fastener device, according to an aspect of the disclosure.

Certain terminology is used in the following description for convenience only and is not limiting. The words "lower" and "upper" designate directions in the drawings to which reference is made. The words "proximally" and "distally" refer to directions toward and away from, respectively, the surgeon using the medical device. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Aspects of the disclosure will now be described in detail with reference to the drawings, wherein like reference numbers refer to like elements throughout, unless specified otherwise. Certain terminology is used in the following description for convenience only and is not limiting. The term "plurality", as used herein, means more than one. The terms "a portion" and "at least a portion" of a structure include the entirety of the structure. Certain features of the disclosure which are described herein in the context of separate embodiments may also be provided in combination in a single embodiment. Conversely, various features of the disclosure that are described in the context of a single embodiment may also be provided separately or in any subcombination.

Reference herein to a first structure articulating along or riding along a second structure refers to the first structure directly contacting the second structure, and precludes an intermediate structure or surface between the first structure and the second structure.

Figure 2:
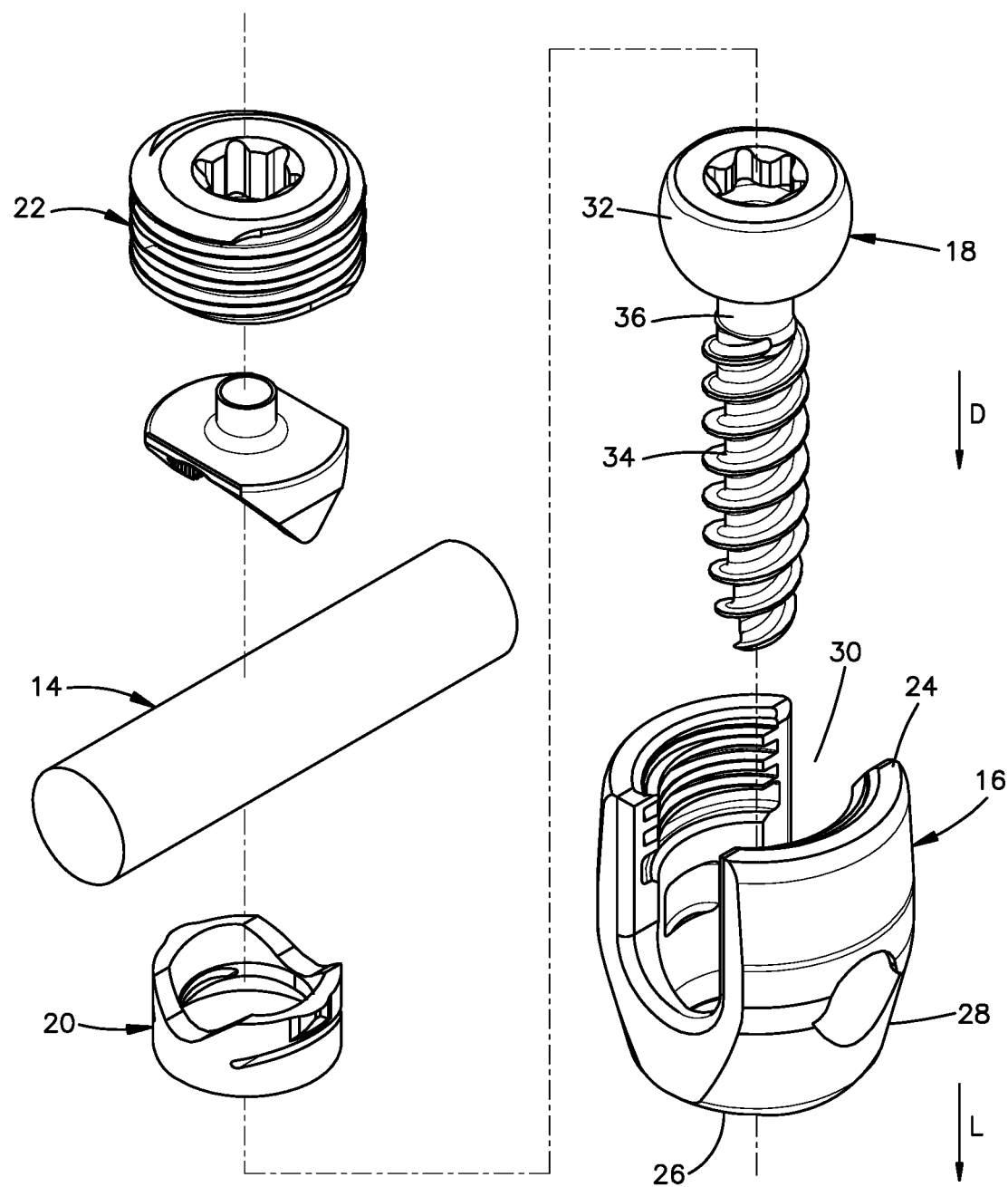
FIG. 2 is an exploded isometric view of the fastener device illustrated in FIG. 1.

Referring to FIGS. 1 and 2 a medical device 10 is configured to secure an elongated member to a portion of a patient's anatomy. As shown in the illustrated embodiment, the medical device 10 can include a fastener device 12 configured to secure a spinal rod 14 to a patient's vertebra, for example a pedicle or lateral mass of the patient's vertebra. The fastener device 12 may be referred to as a pedicle screw when the fastener device 12 is configured to secure the spinal rod 14 to the pedicle of the patient's vertebra. According to one aspect of the disclosure, the fastener device 12 includes an anchor body 16 configured to receive the spinal rod 14, and a fastener 18 configured to be inserted into the anchor body 16 and secured to the patient's vertebra.

The fastener device 12 may further include a saddle 20 and a cap 22. As shown in the illustrated embodiment the saddle 20 is configured to abut both the fastener 18 and the spinal rod 14, and the cap 22 is configured to secure the spinal rod 14 relative to the fastener device 12, as described in further detail below.

According to one aspect of the disclosure, the anchor body 16 includes an upper end 24, a lower end 26 spaced from the upper end 24 in a longitudinal direction L, and an anchor body housing 28 that extends from the upper end 24 to the lower end 26. The anchor body 16 defines a through hole 30 that extends through the anchor body housing 28. The fastener 18 includes a head 32, a threaded shaft 34 that extends out with respect to the head 32 in a distal direction D, and a neck 36 that extends between the head 32 and the threaded shaft 34. The fastener 18 is configured to be positioned into the anchor body 16 by moving the fastener 18 in the longitudinal direction L, until the threaded shaft 34 passes through the lower end 26 and the head 32 is positioned within the through hole 30.

The fastener device 12 is configured such that when the head 32 is positioned in the through hole 30 the fastener 18 is movable, polyaxially, with respect to the anchor body 16. When the head 32 is positioned in the through hole 30, the saddle 20 can be moved in the longitudinal direction L, until the saddle 20 contacts the head 32. When the saddle 20 is contacting the head 32, the spinal rod 14 can then be moved in the longitudinal direction L until the spinal rod 14 contacts the saddle 20. When the spinal rod 14 is contacting the saddle 20, the cap 22 can be moved in the longitudinal direction L until the cap 22 contacts the spinal rod 14.

The cap 22 can include a single piece, or as shown in the illustrated embodiment, a multiple piece, for example two-pieces. The cap 22 includes threads 38, for example external threads, that are configured to threadingly engage with threads 40, for example internal threads, of the anchor body 16. The cap 22 is rotated in a first direction of rotation about an axis, for example an axis parallel to the longitudinal direction L, such that the threads 38 engage with the threads 40 and the cap 22 moves in the longitudinal direction L with respect to the anchor body 16. According to one embodiment, the cap 22 is configured to be rotated until the cap 22 is no longer rotatable in the first direction of rotation when a set torque is applied to the cap 22, thereby securing the spinal rod 14 to the fastener device 12 such that relative movement of the spinal rod 14 and the fastener device 12 is limited, for example prevented, and thereby securing the fastener 18 to the anchor body 16 such that relative movement of the fastener 18 and the anchor body 16 is limited, for example prevented. According to one embodiment, the set torque is between about 2 Newton-meters (N-m) and about 3 N-m.

Figure 5:
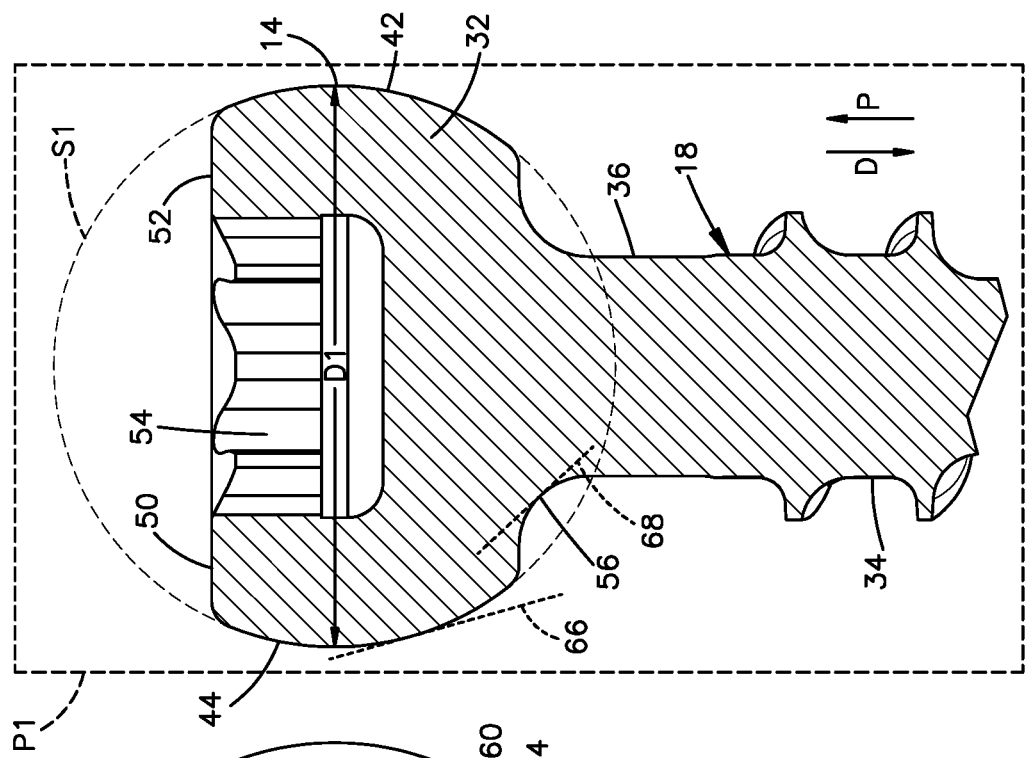
FIG. 5 is a cross-sectional view of the fastener illustrated in FIG. 3, along line 5-5.
Figure 4:
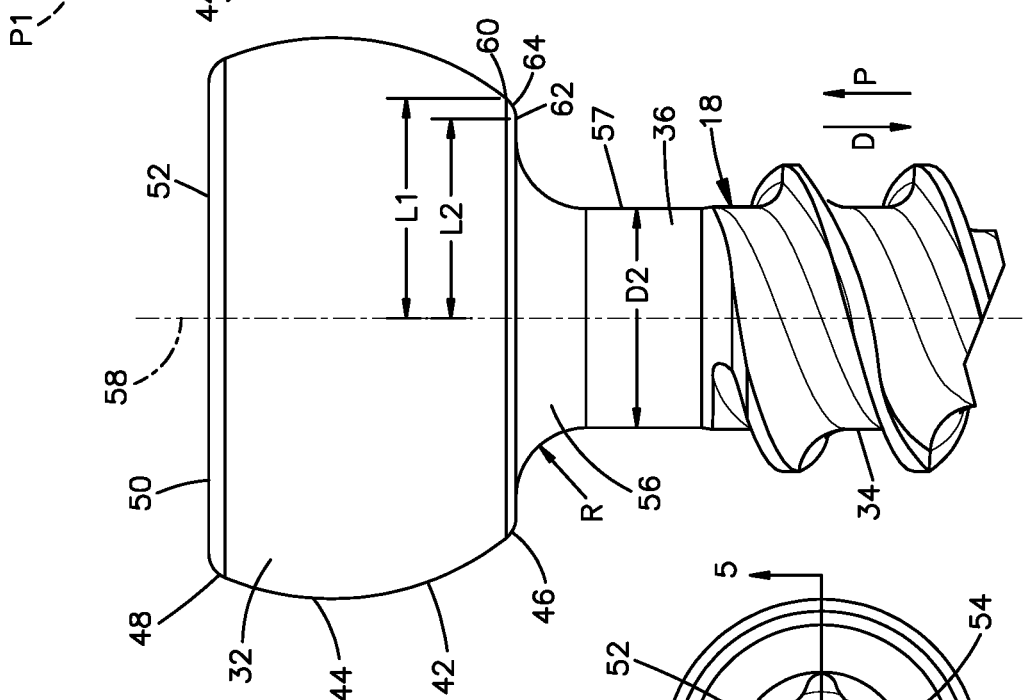
FIG. 4 is a side elevation view of the fastener illustrated in FIG. 3.
Figure 3:
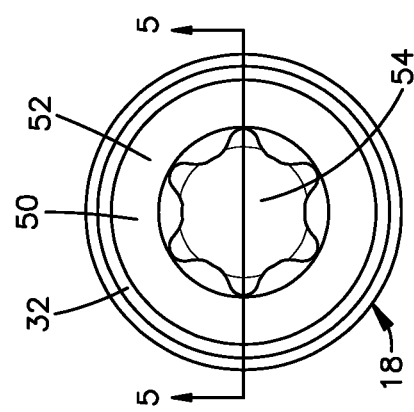
FIG. 3 is a top plan view of a fastener of the fastener device illustrated in FIG. 1.

Referring to FIGS. 3 to 5, the head 32 of the fastener 18 includes an outer surface 42. According to one aspect of the disclosure, a portion 44 of the outer surface 42 may be convex, may define a portion of a first sphere S1, or both. The first sphere S1 defines a first diameter D1. According to one aspect of the disclosure, the first diameter D1 may be greater than about 4.5 mm. According to another aspect of the disclosure, the first diameter D1 may be greater than about 5.0 mm. According to another aspect of the disclosure, the first diameter D1 may be in a range between about 5.0 mm and about 8.0 mm. According to another aspect of the disclosure, the first diameter D1 may be about 6.0 mm.

The outer surface 42 may include one or more additional portions that do not define a portion of the first sphere S1. As shown in the illustrated embodiment, the outer surface 42 may include a distal portion 46 that is positioned in the distal direction D with respect to the portion 44, a proximal portion 48 that is positioned in a proximal direction P, which is opposite the distal direction D, with respect to the portion 44, or both the distal portion 46 and the proximal portion 48. According to another aspect of the disclosure, an entirety of the outer surface 42 may include the portion 44, such that the outer surface 42 is devoid of the distal portion 46 and the proximal portion 48.

The head 32 of the fastener 18 may define a location 50 such that the fastener 18 is devoid of any locations positioned in the proximal direction P from the location 50. As shown in the illustrated embodiment, the head 32 includes an upper surface 52 that defines a drive mechanism 54, the drive mechanism 54 configured to receive a driving force that rotates the fastener 18 to secure the fastener 18 to a vertebra. According to one aspect of the disclosure, the upper surface 52 can be substantially flat, such that any point on the upper surface 52 can define the location 50. According to another aspect of the disclosure, the upper surface 52 can be not flat, for example curved such that an apex of the upper surface 52 defines the location 50.

According to one aspect of the disclosure, the fastener 18 may include a surface 56 that extends along both the head 32 and the neck 36. As shown in the illustrated embodiment, the surface 56 may be concave such that the surface 56 defines a radius of curvature R. According to one embodiment, the radius of curvature R may be constant along an entirety of the surface 56. For example, the surface 56 may define a radius of curvature R of between about 0.25 mm and about 2.0 mm. According to another example, the surface 56 may define a radius of curvature R of between about 0.4 mm and about 1.0 mm. According to another embodiment, the radius of curvature R may vary along the surface 56. According to another embodiment, the surface 56 may include two perpendicular surfaces such that the surface 56 does not define a radius of curvature R.

The portion of the fastener 18 between the head 32 and the shaft 34, for example the neck 36, is a potential area where the fastener 18 may fail under load. According to one aspect of the disclosure, radius of curvature R of the concave surface 56, may distribute stresses within the fastener 18, thereby increasing the effective strength of the fastener 18. For example, a first fastener 18 that defines a first radius of curvature R that is larger than a second radius of curvature defined by a second fastener 18 may result in a better distribution of stresses under load in the first fastener 18 when compared to the second fastener 18, and thus the first fastener 18 may have an increased effective strength compared to the second fastener 18.

According to one aspect of the disclosure, the neck 36 defines a second diameter D2 that may be measured both in a direction perpendicular to the distal direction D and at a location 57 that is in the distal direction D with respect to the surface 56. As shown in the illustrated embodiment, the second diameter D2 may be measured both in the distal direction D and at the location 57 which is in the distal direction D with respect to an entirety of the surface 56 which defines the radius of curvature R. The second diameter D2 may be constant such that the second diameter D2 at first and second locations spaced apart with respect to the distal direction D, is the same. Alternatively, the second diameter D2 may vary, for example decrease in the distal direction D2.

According to another aspect of the disclosure, the second diameter D2 may be in a range between about 1.0 mm and about 4.0 mm. According to another aspect of the disclosure, the second diameter D2 may be about 2.5 mm. The fastener 18 defines a ratio of the first diameter D1 to the second diameter D2. According to one aspect of the disclosure, the ratio of the first diameter D1 to the second diameter D2 is in a range between about 2 to 1 and about 3 to 1.

The fastener 18 may be elongate along an axis, for example a central fastener axis 58. As shown in the illustrated embodiment, the central fastener axis 58 is parallel to the distal direction D. According to one aspect of the disclosure, the portion 44 of the outer surface 42 may include a first point 60 that is located in the distal direction with respect to all other points of the portion 44 of the outer surface 42, the surface 56 includes a second point 62 that is located in the proximal direction P with respect to all other points of the surface 56, the first point 60 is spaced from the central fastener axis 58 a first distance L1 measured in a direction perpendicular to the distal direction D, the second point 62 is spaced from the central fastener axis 58 a second distance L2 measured in a direction perpendicular to the distal direction D, and the first distance L1 is greater than the second distance L2.

The head 32 may include an intermediate surface 64 that extends between the surface 56 and the outer surface 42. According to one aspect of the disclosure, at least a portion of the intermediate surface 64 may be substantially flat and perpendicular to the distal direction D.

The fastener 18 may be configured such that all lines that both lie entirely within a plane P1 that is parallel to the distal direction D and that are tangent to the portion 44 of the outer surface 42 are noncollinear with all lines that both lie entirely within the plane P1 and that are tangent to the surface 56. For example, a line 66 which both lies entirely within the plane P1 and is tangent to the portion 44 is not collinear with a line 68 which both lies entirely within the plane P1 and is tangent to the surface 56.

Referring to FIGS. 6 and 7, the anchor body 16 may define a rod-receiving channel 69 that is configured to receive a spinal rod, for example the spinal rod 14 (as shown in FIG. 1). The rod-receiving channel 69 extends through the anchor body housing 28 and may be oriented such that the rod-receiving channel 69 is offset from, for example perpendicular to, the through hole 30. As shown in the illustrated embodiment, the rod-receiving channel 69 may be a U-shaped channel.

The anchor body 16 may further include an inner surface 70 that defines at least a portion of the through hole 30. According to one aspect of the disclosure, a portion 72 of the inner surface 70 may be concave, may define a portion of a second sphere S2, or both. The second sphere S2 defines a third diameter D3. According to one aspect of the disclosure, the third diameter D3 is equal to the first diameter D1. According to another aspect of the disclosure, the third diameter D3 is either greater than or less than the first diameter D1.

The inner surface 70 defines a minimum inner diameter D4 that is measured both in a direction perpendicular to the longitudinal direction L and at a location 74 that is closer to the lower end 26 as measured along the longitudinal direction L than the location 74 is to the upper end 24 as measured along the longitudinal direction L. As shown in the illustrated embodiment, the location 74 may be spaced a distance from the lower end 26 measured along the longitudinal direction L, such that the inner surface 70 tapers radially outward with respect to a central anchor body axis 76 as the inner surface 70 extends from the location 74 to the lower end 26. According to another aspect of the disclosure, the location 74 may be located at the lower end 26. According to one embodiment, the location 74 may be positioned on the portion 72 such that no point on the portion 72 is positioned in the longitudinal direction L with respect to the location 74.

The anchor body 16 defines an inner diameter D5 that is greater than the minimum inner diameter D4. According to one aspect of the disclosure, the inner diameter D5 may be defined by the inner surface 70 at a location that is spaced from the portion 72 in a direction opposite the longitudinal direction L. According to another aspect of the disclosure, the inner diameter D5 may be defined by the upper end 24. According to one aspect of the disclosure, the inner diameter D5 may be a maximum inner diameter of the anchor body 16.

According to one aspect of the disclosure, the upper end 24 defines an upper opening 78 where the through hole 30 exits the anchor body housing 28 in the direction opposite the longitudinal direction L, the lower end 26 defines a lower opening 80 where the through hole 30 exits the anchor body housing 28 in the longitudinal direction L, or both. As shown in the illustrated embodiment, the anchor body 16 may define a plane P2 (shown as a line which extends into and out of the page). The plane P2 may include an entirety of the lower opening 80, may be perpendicular to the longitudinal direction L, or both.

Figure 8:
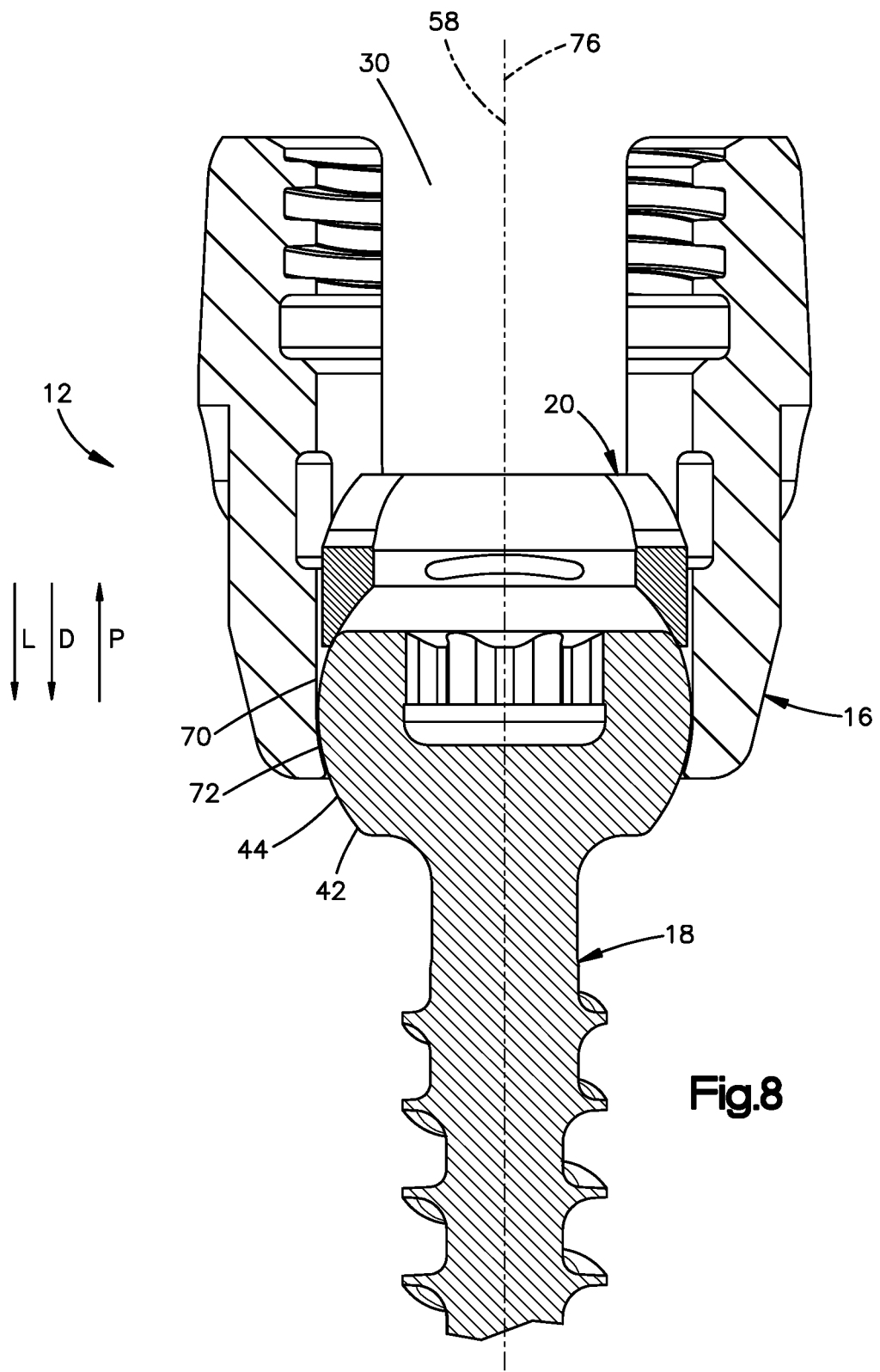
FIG. 8 is a cross-sectional view of the fastener device illustrated in FIG. 1, along line 8-8, the fastener device in a first configuration.
Figure 9:
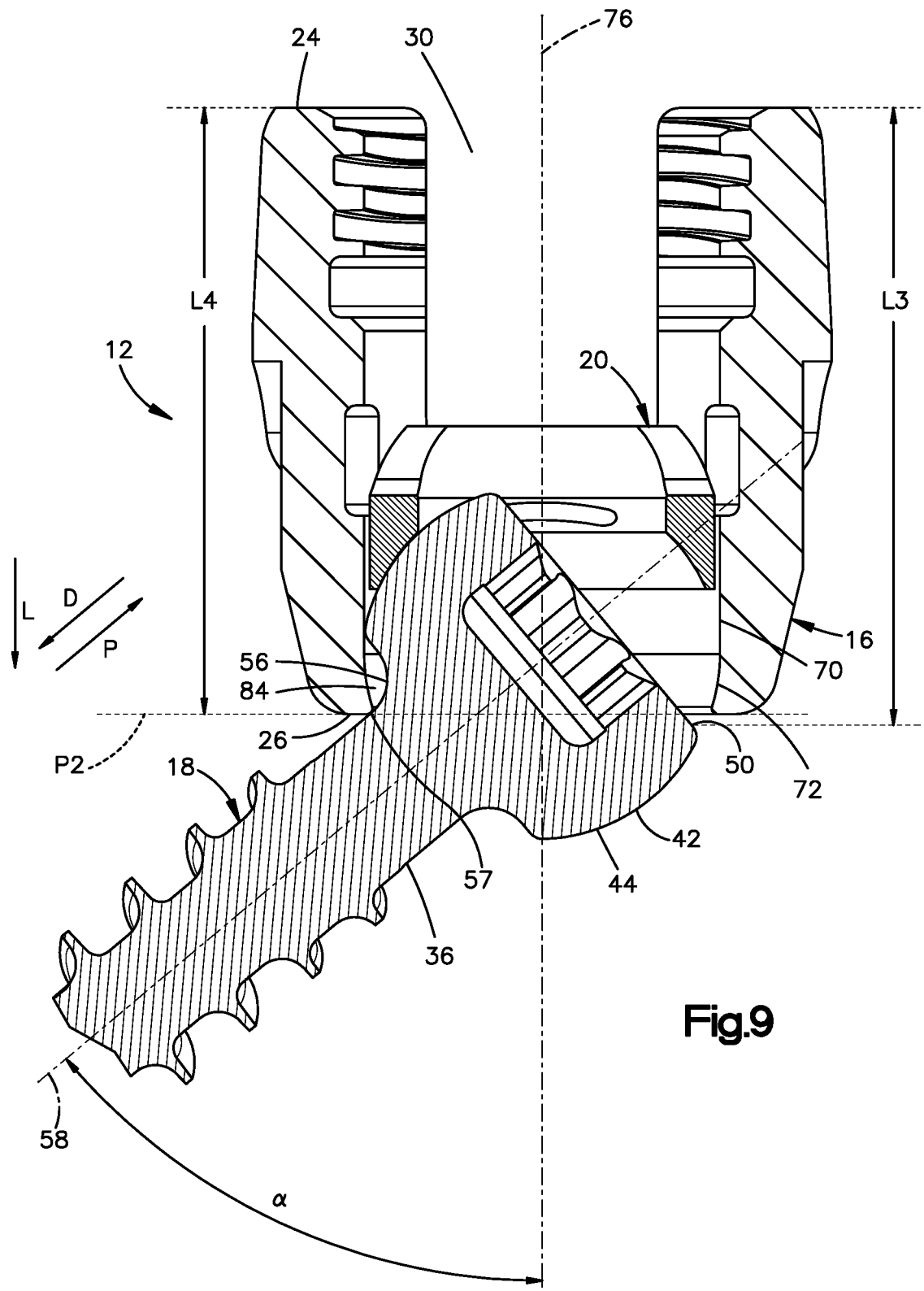
FIG. 9 is a cross-sectional view of the fastener device illustrated in FIG. 1, along line 8-8, the fastener device in a second configuration.

Referring to FIGS. 8 and 9, the fastener device 12 defines an assembled configuration in which the portion 44 of the outer surface 42 rides along (contacts at more than one point) the portion 72 of the inner surface 70 such that the fastener 18 is movable with respect to the anchor body 16. The contact between the portion 44 and the portion 72 may define a circle, a portion of a circle, a portion of a sphere, or any combination thereof. According to one aspect of the disclosure, the fastener 18 is movable polyaxially with respect to the anchor body 16 such that the fastener device 12 defines a cone of angulation that includes all of the angles at which the central fastener axis 58 and the central anchor body axis 76 can be offset from one another when the fastener device 12 is in the assembled configuration. The cone of angulation may be defined by a maximum angle α (alpha), for example the cone of angulation may be twice the maximum angle α (alpha).

The maximum angle α (alpha) is measured between the central fastener axis 58 and the central anchor body axis 76 when the anchor body 16 abuts the neck 36 at a location that is spaced in the distal direction D from an entirety of the surface 56 such that movement of the fastener 18 relative to the anchor body 16 in at least one direction is blocked.

According to one aspect of the disclosure the maximum angle α (alpha) is greater than about 45 degrees. According to another aspect of the disclosure the maximum angle α (alpha) is greater than about 50 degrees. According to another aspect of the disclosure the maximum angle α (alpha) is between about 50 degrees and about 60 degrees. For example, the fastener device 12 may be configured as a cervical fastener device with a maximum angle α (alpha) of about 50 degrees. As another example the fastener device 12 may be configured as a lumbar fastener device with a maximum angle α (alpha) of about 30 degrees.

As shown in FIG. 8, when the fastener device 12 is in the configuration the central fastener axis 58 and the central anchor body axis 76 may be parallel, for example collinear. As shown in FIG. 9, when the fastener device 12 is in the configuration the central fastener axis 58 and the central anchor body axis 76 may be angularly offset, for example by the maximum angle α (alpha) or by any angle less than maximum angle α (alpha).

Referring to FIGS. 5, 7, and 8, because the first diameter D1 is larger than the minimum inner diameter D4 the head 32 of the fastener 18 is not able to be inserted into the through hole 30 along the direction opposite the longitudinal direction L such that the portion 44 of the outer surface 42 rides along the portion 72 of the inner surface 70. Instead, because the inner diameter D5 is greater than the first diameter D1, the fastener 18 is configured to be inserted into the through hole 30 along the longitudinal direction L such that the portion 44 of the outer surface 42 rides along the portion 72 of the inner surface 70. Thus the fastener device 12 can be described as a top-loading fastener device as opposed to a bottom-loading (or pop-on) fastener device. The fastener device 12 being configured as a top-loading fastener device allows the size of the first diameter D1 and the size of the second diameter D2 to remain larger than in a comparable bottom-loading screw, which can result in a fastener device 12, and specifically a fastener 18, with increased strength.

Referring to FIG. 9, according to one aspect of the disclosure the fastener device 12 defines a configuration in which the location 50 is positioned a third distance L3 from the upper end 24 measured along the longitudinal direction L, the lower end 26 is positioned a fourth distance L4 from the upper end 24 measured along the longitudinal direction L, and the third distance L3 is greater than the fourth distance L4. According to one aspect of the disclosure the fastener device 12 defines a configuration in which the location 50 is spaced in the longitudinal direction L with respect to the plane P2.

According to one aspect of the disclosure, the fastener device 12 defines a configuration (referred to herein as a maximum angled configuration) in which both the portion 44 of the outer surface 42 rides along the portion 72 of the inner surface 70, and the anchor body 16 abuts the neck 36 at the location 57 that is spaced in the distal direction D from an entirety of the surface 56 such that movement of the fastener 18 relative to the anchor body 16 in at least one direction is blocked.

Referring to FIGS. 8 and 9, the fastener device 12 is illustrated with the saddle 20 abutting the fastener 18, and the spinal rod 14 and the cap 22 are not shown. The description of FIGS. 8 and 9 applies to the fastener device 12 with and without any combination of the saddle 20, the cap 22, and the spinal rod 14.

As shown in the illustrated embodiment, when the fastener device 12 is in the maximum angled configuration a gap 84 is defined between the surface 56 and the anchor body 16. The gap 84 is enclosed in both the longitudinal direction L and the direction opposite the longitudinal direction L. According to one aspect of the disclosure, when the fastener device is in the maximum angled configuration, a region of contact that includes all of the points of contact between the anchor body 16 and the fastener 18 as measured in a plane that is perpendicular to the longitudinal direction L defines a portion of a circle that is less than a full circle.

Referring to FIGS. 4 and 9, according to one aspect of the disclosure the strength of the fastener 18 may be increased by maximizing the second diameter D2. However, increasing the size of the second diameter D2 while not changing other dimensions of the fastener 18, for example the first diameter D1, may result in a fastener device 12 with a lower maximum angle α (alpha). Accordingly, maximizing the second diameter D2 while maintaining the ratio of the first diameter D1 to the second diameter D2 may result in a fastener 18 with increased strength and a fastener device 12 with a greater maximum angle α (alpha). According to one aspect of the disclosure the strength of the fastener 18 may be increased by increasing the size of the radius of curvature R. The increased size of the radius of curvature R may result in less material being present in the area between the head 32 and the threaded shaft 34, however the large radius of curvature may reduce stress concentrations within the area between the head 32 and the threaded shaft 34, thereby resulting in increased strength of the fastener 18.

Additionally, in the fastener device 12 as shown in the illustrated embodiment the portion 44 of the outer surface 42 articulates along or rides along the portion 72 of the inner surface 70 such that the portion 44 directly contacts the portion 72. According to the illustrated embodiment, the fastener device may be devoid of a collet or other intermediate structure between the portion 44 and the portion 72. The inclusion of a collet or other intermediate structure positioned within the through hole 30 of a given size would result in the use of a fastener with a first diameter D1 being smaller than the first diameter D1 of the fastener 18 which is configured for use with the fastener device 12 that is devoid of a collet or other intermediate structure. Thus, the fastener device 12 being devoid of a collet or other intermediate structure between the portion 44 and the portion 72 may result in increased strength in the fastener 18 configured for use with the fastener device 12.

Referring to FIGS. 1 to 9, a method of making the fastener device 12 may include the step of inserting the fastener 18 into the anchor body 16 such that the threaded shaft 34 passes through the lower opening 80 of the anchor body 16. The method of making the fastener device 12 may further include the steps of: inserting the saddle 20 into the anchor body 16; inserting the spinal rod 14 into the anchor body 16; inserting the cap 22 into the anchor body 16; or any combination thereof.

The method of making the fastener device 12 may further include the step of tightening the cap 22. According to one aspect of the disclosure, the fastener device 12 is configured such that after the step of inserting the fastener 18 into the anchor body 16, and before the tightening step the fastener 18 is freely movable within the through hole 30 with respect to the anchor body 16, and vice versa. The fastener 18 being freely movable includes the fastener 18 being translatable with respect to the anchor body 16 along the longitudinal direction L, the fastener 18 being polyaxially rotatable with respect to the anchor body 16, or both.

Figure 10:
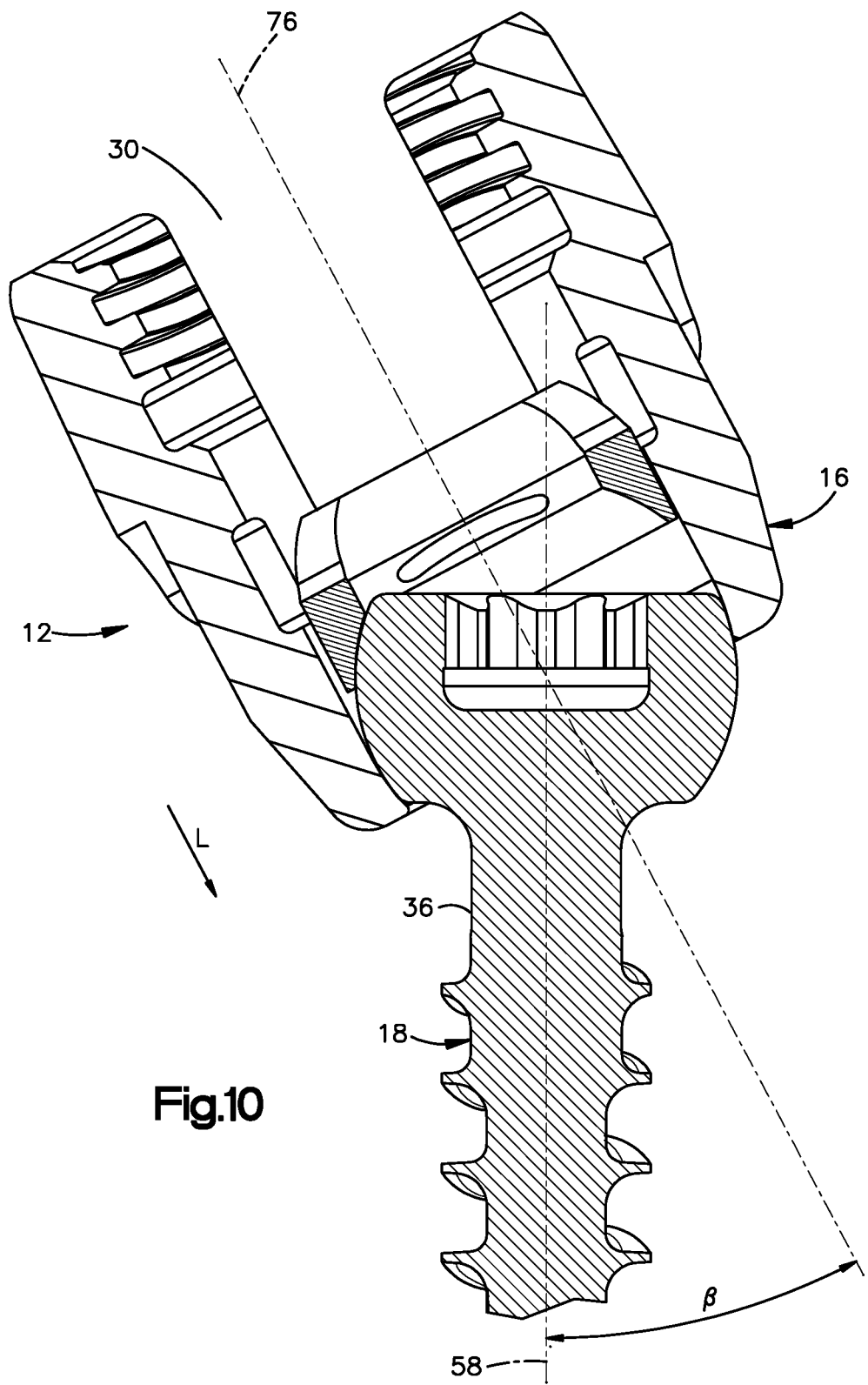
FIG. 10 is a cross-sectional view of the fastener device illustrated in FIG. 1, along line 8-8, the fastener device in a third configuration.
Figure 11:
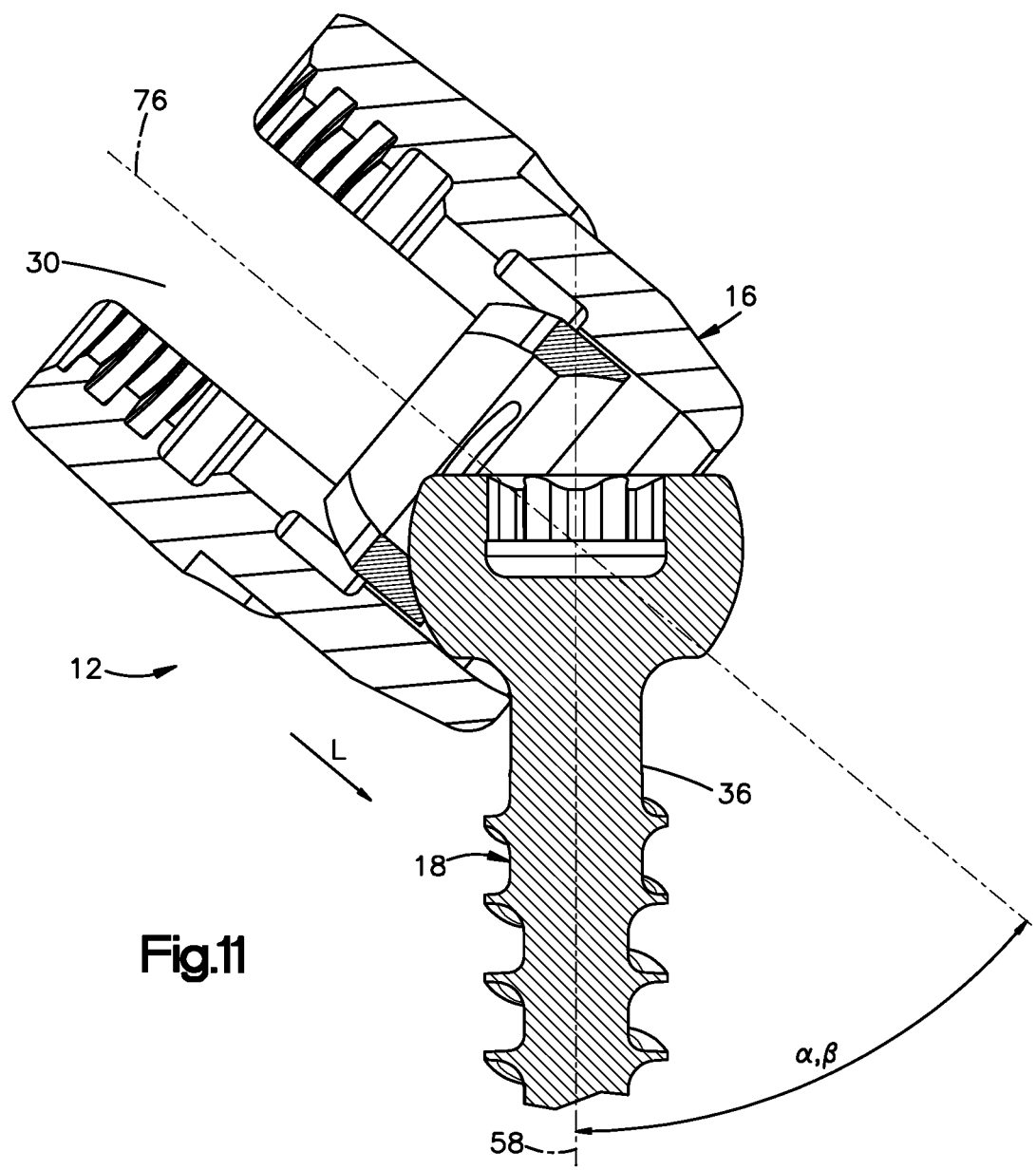
FIG. 11 is a cross-sectional view of the fastener device illustrated in FIG. 1, along line 8-8, the fastener device in the second configuration.
Figure 12:
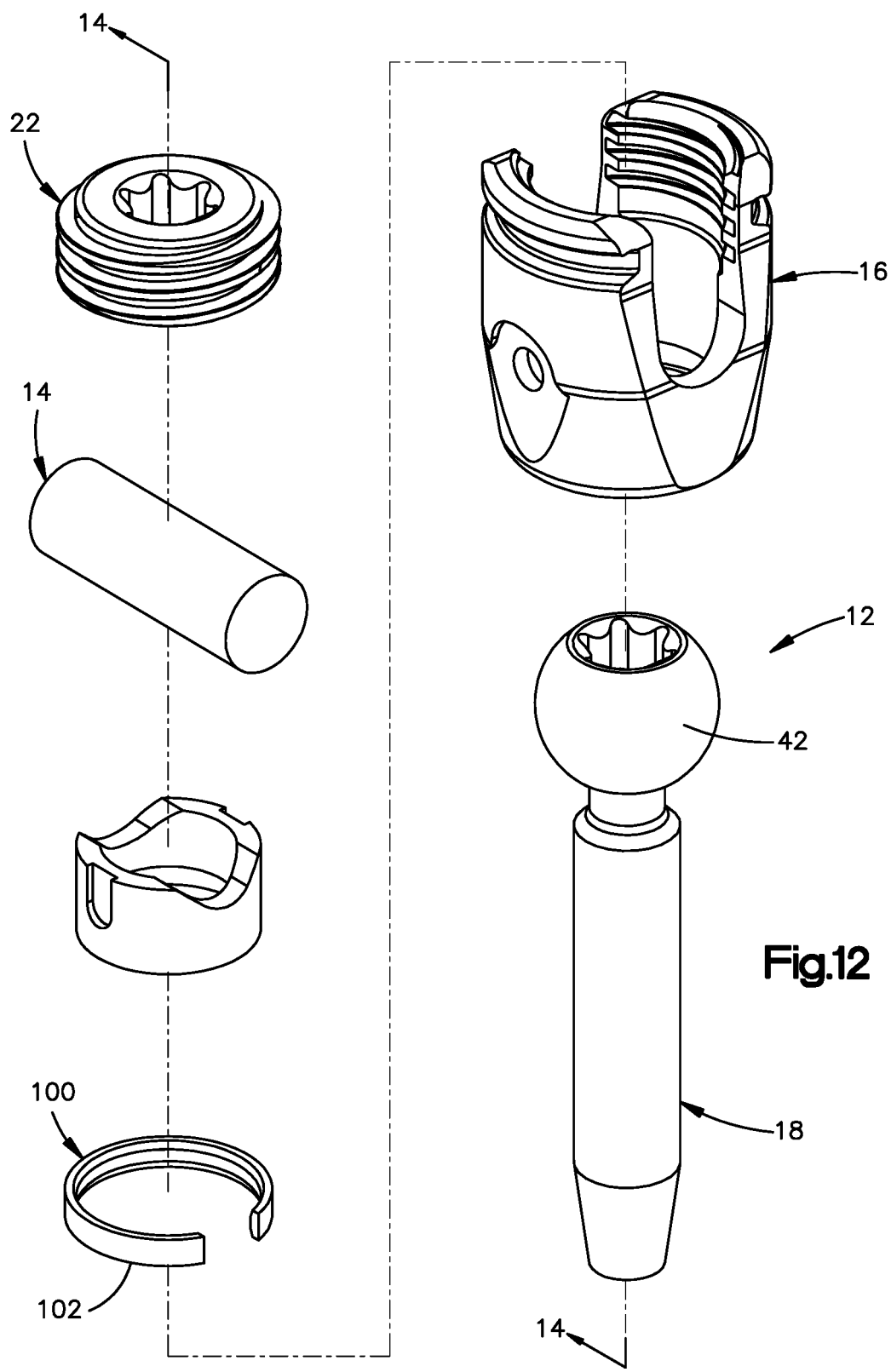
FIG. 12 is an exploded isometric view of a fastener device according to an aspect of the disclosure, the fastener device including a biasing member and an anchor body.

Referring to FIGS. 10 and 11, the fastener 18 being freely movable within the through hole 30 with respect to the anchor body 16 may result in undesired movement of the anchor body 16 relative to the fastener 18 during insertion of the fastener 18 into hole 30. As shown in the illustrated embodiment of FIG. 10, during insertion, the fastener 18 and the anchor body 16 may be offset with respect to the longitudinal direction L, for example the central fastener axis 58 and the central anchor body axis 76 may be angularly offset by an angle, β (beta). The angular offset of the central fastener axis 58 and the central anchor body axis 76 may result in a force, such as the force of gravity on the anchor body 16, being sufficient to move the anchor body 16 relative to the fastener 18, for example until the neck 36 of the fastener 18 contacts the anchor body 16, as shown in FIG. 11.

Referring to FIGS. 12 to 17, the fastener device 12 may include a biasing member 102 configured to restrict, for example by providing a force, relative movement of the anchor body 16 and the fastener 18 after the fastener 18 is inserted into the anchor body 16, and before the cap 22 is inserted into the through hole 30 such that the cap 22 abuts the spinal rod 14.

Biasing member 102 may be disposed in a recess 106 in anchor body 16 such that movement of the biasing member 102 relative to the anchor body 16 is limited in a direction, for example a direction parallel to the central anchor body axis 76. The biasing member 102 may further be configured to provide a force on the outer surface 42 of the fastener 18. As shown in the illustrated embodiment, the biasing member 102 may be a split ring. According to another embodiment, the biasing member 102 may be a non-circular shape, such as but not limited to a polygonal shape. As shown in the illustrated embodiment, the recess 106 may be defined by the anchor body 16.

According to one aspect of the disclosure, the biasing member 102 may be configured to expand radially with respect to the central anchor body axis 76. For example, before the fastener 18 is inserted into the through hole 30, the biasing member 102 defines an inner diameter D6 having a first dimension. The biasing member 102 may be configured to expand as the fastener 18 is inserted into the through hole 30, and the outer surface 42 of the fastener contacts the biasing member 102. Once the fastener 18 is fully seated within the through hole 30, such that no further movement of the fastener 18 in the longitudinal direction L relative to the anchor body 18, is possible due to the outer surface 42 abutting the inner surface 70, the inner diameter D6 has a second dimension that is larger than the first dimension. The biasing member 102 is configured such that increasing the size of the inner diameter D6 imparts a force on the outer surface 44 of the fastener 18. According to one aspect of the disclosure, the fastener device 12 is configured such that the biasing member 102 imparts the force on the outer surface 42 in a direction substantially perpendicular to the central anchor body axis 76.

Referring to FIG. 13, the biasing member 102 includes an inner surface 112 and an outer surface 114. As shown in the illustrated embodiment, the inner surface 112 defines a through hole 115 that extends through the biasing member 100. The inner surface 112 may define at least a portion, for example greater than half of, a circle. The circle of which at least a portion is defined by the inner surface 112 may include a center 116. The inner diameter D6 is measured along a straight line from a first point on the inner surface 112, through the center 116, to a second point on the inner surface 112 spaced apart from the first point.

The biasing member 102 may further define an outer diameter D7 measured along a straight line from a first point on the outer surface 114, through the center 116, to a second point on the outer surface 114 spaced apart from the first point on the outer surface 114. The outer diameter D7 is greater than the inner diameter D6.

Referring to FIG. 14, the inner surface 70 of the anchor body 16 defines the recess 106. The recess 106 extends radially into the inner surface 70 of the anchor body 16 and terminates at a base surface 118. The recess 106 further extends into the inner surface 70 of the anchor body 16 such that the recess 106 defines a recess height RH. The recess height RH is measured along a straight line that is parallel to the central anchor body axis 76 from a recess upper surface 120 to a recess lower surface 122. The anchor body 16 defines an inner diameter D8 measured along a straight line that is perpendicular to the central anchor body axis 76 from a first point on the base surface 118, through the central anchor body axis 76, to a second point on the base surface 118 that is spaced from the first point.

The anchor body 16 further defines an inner diameter D9 measured along a straight line that is perpendicular to the central anchor body axis 76 from a first point on the inner surface 70 that is offset from the recess in the direction opposite the longitudinal direction L, through the central anchor body axis 76, to a second point on the inner surface 70 that is spaced from the first point. The anchor body 16 further defines an inner diameter D10 measured along a straight line that is perpendicular to the central anchor body axis 76 from a first point on a portion 86 of the inner surface 70 that is offset from the recess in the longitudinal direction L, through the central anchor body axis 76, to a second point on the portion 86 of the inner surface 70 that is spaced from the first point. According to one aspect of the disclosure, the inner diameter D8 is larger than both the inner diameter D9 and the inner diameter D10. As shown in the illustrated embodiment, the portion 86 may be curved and define a portion of a sphere having a diameter.

Figure 15:
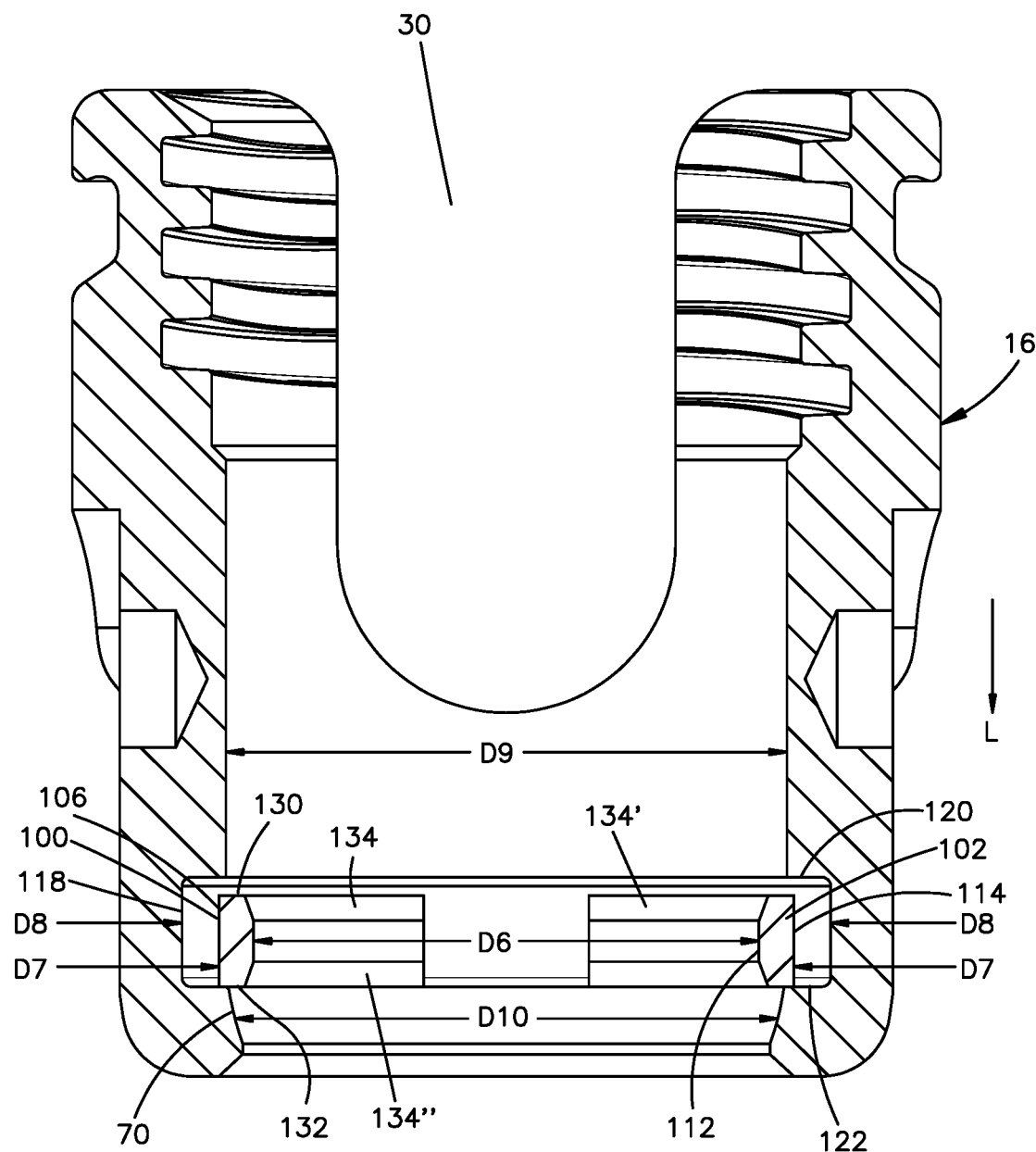
FIG. 15 is a cross-sectional view of the biasing member and the anchor body illustrated in FIG. 12, along line 14-14, the biasing member and the anchor body in an assembled configuration.

Referring to FIGS. 12 to 15, the biasing member 102 includes an unbiased state when the fastener 18 is not abutting the inner surface 112 and the anchor body 16 is not abutting the outer surface 114. The biasing member 102 further includes a biased state when the fastener 18 is abutting the inner surface 112, the anchor body 16 is abutting the outer surface 114, or both. The fastener device 12 may be configured such that the biasing member 102 is configured to be positioned within the recess 106. According to one aspect of the disclosure, the biasing member 102 is configured to be in the unbiased state when positioned within the recess 106, and the recess 106 is configured to retain the biasing member 102 within the recess 106, as shown in FIG. 15.

As shown in the illustrated embodiment, the fastener device 12 may be configured such that, in the unbiased state, the inner diameter D6 is smaller than both the inner diameter D9 and the inner diameter D10, the outer diameter D7 is larger than both the inner diameter D9 and the inner diameter D10, and the inner diameter D8 is larger than the outer diameter D7. The biasing member 102, in the unbiased state, is disposed within the recess 106 such that movement of the biasing member 102 out of the recess along the longitudinal direction L is blocked by the upper surface 120 and the lower surface 122. The recess 106 further provides room for the biasing member 102 to expand radially out toward the base surface 118.

The biasing member 102 may further include a top surface 130 and a bottom surface 132 opposite the top surface 130. As shown in the illustrated embodiment, the bottom surface 132 faces in the longitudinal direction L and the top surface 130 faces in the direction opposite the longitudinal direction L. The biasing member 102 may further include one or more tapered surfaces 134. The one or more tapered surfaces 134 may include a first tapered surface 134' that extends between the upper surface 130 and the inner surface 112, a second tapered surface 134" that extends between the lower surface 132 and the inner surface 112, or both. The one or more tapered surfaces 134 may be linear, curved, or partially linear and partially curved. The one or more tapered surfaces 134 are configured to enable easier entry of the fastener 18 into the through hole 115, for example by lowering the amount of force required compared to a biasing member 102 devoid of the one or more tapered surfaces 134.

Referring to FIG. 16, the fastener 18 is configured to be inserted into the through hole 30 such that the threaded shaft 34 extends through the lower opening 80 and the outer surface 42 abuts the inner surface 112, thereby transitioning the biasing member 102 into a biased state. The fastener device 12 may define a fully seated configuration in which the outer surface 42 abuts the portion 86 of the inner surface 70. When the fastener device 12 is in the fully seated configuration the biasing member 102 exerts a force on the fastener 18, and that force resists relative to movement of the fastener 18 and the anchor body 16.

Relative movement of the fastener 18 and the anchor body 16 along the longitudinal direction L is resisted by the biasing member 102, which is exerting an inward radial force on the fastener 18, abutting either the upper surface 120 or the lower surface 122. Relative rotation, for example polyaxial rotation, of the fastener 18 and the anchor body 16 is resisted by a drag force or friction force resulting from the inward radial force exerted by the biasing member 102 on the fastener 18.

According to one aspect of the disclosure, the fastener 18 defines a widest location 136 that is larger, as measured along a straight line perpendicular to the central fastener axis 58 from a first point on the outer surface 42, through the central fastener axis 58, to a second point on the outer surface 42, than any other location on the head 32. The fastener device 12 may be configured such that in the fully seated configuration, when the central fastener axis 58 is parallel to the central anchor body axis 76, the biasing member 102 abuts the outer surface 42 at a location aligned with the widest location 136 with respect to the distal direction D.

According to another embodiment, the fastener device 12 may be configured such that in the fully seated configuration, when the central fastener axis 58 is parallel to the central anchor body axis 76, the biasing member 102 abuts the outer surface 42 at a location either spaced from the widest location 136 in the distal direction D, or spaced from the widest location 136 in the proximal direction P.

The method of making the fastener device 12 may include the step of inserting the fastener 18 into the biasing member 102 until the outer surface 42 abuts the portion 86 of the inner surface 70. The above step of inserting the fastener 18 into the biasing member 102 may include the step of radially expanding the biasing member 102 such that the inner diameter D6 increases. The above step of inserting the fastener 18 into the biasing member 102 may further include, after the step of radially expanding the biasing member 102, the step of radially contracting the biasing member 102 such that the inner diameter D6 decreases.

Referring to FIG. 17, the biasing member 102 is configured to resist undesired relative movement of the fastener 18 and the anchor body 16, but allow desired relative movement of the fastener 18 and the anchor body 16. In use, when the fastener 18 is in the fully seated configuration, the anchor body 16 may be moved relative to the fastener 18, for example by a surgeon manipulating at least one of the fastener 18 and the anchor body 16. Additionally, when the fastener 18 is in the fully seated configuration, the biasing member 102 prevents relative movement of the anchor body 16 relative to the fastener 18, for example due to gravity acting on the anchor body 16 when the central fastener axis 58 is angular offset from the central anchor body axis 76 by the angle β (beta). According to one aspect of the disclosure, the angle β (beta) may be between 0 and the maximum angle α (alpha).

The description of the biasing member 102 illustrated in FIGS. 12 to 17 also applies to the embodiments illustrated in FIGS. 1 to 11. Additionally, the description of the embodiments illustrated in FIGS. 1 to 11 is applicable to the embodiments illustrated in FIGS. 12 to 17.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range including the stated ends of the range, unless otherwise indicated herein, and each separate value is incorporated into the specification as if it were individually recited herein. All methods described herein can be performed in any suitable order unless otherwise indicated herein or otherwise clearly contradicted by context.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

We claim:

1. A fastener device configured to secure a spinal rod relative to a bone, the fastener device comprising:
    an anchor body including an anchor body housing, the anchor body defining a through hole that extends through the anchor body housing, the anchor body further defining a rod-receiving channel that is configured to receive the spinal rod, the anchor body further including an upper end, a lower end, and an inner surface, the inner surface defining a least a portion of the through hole; and
    a fastener including a head, a threaded shaft that extends out with respect to the head in a distal direction, and a neck that extends between the head and the threaded shaft, the head including an outer surface configured to articulate along the inner surface when the fastener head is inserted in the through hole, at least a portion of the outer surface being convex and defining a portion of a sphere, the sphere defining a first diameter, and the fastener including a concave surface that extends along both the head and the neck, the neck defining a second diameter measured: 1) in a direction perpendicular to the distal direction, and 2) at a location spaced in the distal direction of an entirety of the concave surface,
    wherein the fastener defines a ratio of the first diameter to the second diameter in a range between about 2 to 1 and about 3 to 1.

2. The fastener device of claim 1, wherein:
    the fastener is elongate along a central axis that is parallel to the distal direction;
    the portion of the outer surface includes a first point that is located in the distal direction with respect to all other points of the portion of the outer surface;
    the concave surface includes a second point that is located in a proximal direction, which is opposite the distal direction, with respect to all other points of the concave surface; and
    the first point is spaced from the central axis a first distance measured in a direction perpendicular to the distal direction, the second point is spaced from the central axis a second distance measured in a direction perpendicular to the distal direction, and the first distance is greater than the second distance.

3. The fastener device of claim 1, wherein the location is a first location, the through hole extends away from the upper end and toward the lower end in a longitudinal direction, and the inner surface defines a minimum inner diameter that is both: 1) measured at a second location that is on the inner surface, and 2) measured in a direction perpendicular to the longitudinal direction, the second location is closer to the lower end as measured along the longitudinal direction, than the second location is to the upper end as measured along the longitudinal direction.

4. The fastener device of claim 3, wherein the lower end defines a lower opening where the through hole exits the anchor body housing, the anchor body defines a plane that includes an entirety of the lower opening, the head of the fastener defines a third location such that the fastener is devoid of any locations positioned in a proximal direction, which is opposite the distal direction, from the third location, and the fastener device defines a configuration in which the third location is positioned a first distance from the upper end, the lower end is positioned a second distance from the upper end, the first distance and the second distance each measured along the longitudinal direction, and the first distance is greater than the second distance.

5. The fastener device of claim 3, wherein the first diameter is larger than the minimum inner diameter.

6. The fastener device of claim 5, wherein the upper end defines an upper opening where the through hole exits the anchor body housing, the upper opening defines an inner diameter measured in the direction perpendicular to the longitudinal direction, and the inner diameter is greater than both the first diameter and the minimum inner diameter.

7. The fastener device of claim 1, wherein all lines that: 1) lie entirely within a plane parallel to the distal direction, and 2) are tangent to the portion of the outer surface are noncollinear with all lines that: 1) lie entirely within the plane, and 2) are tangent to the concave surface.

8. The fastener device of claim 1, further comprising a stabilization mechanism configured to be positioned in the through hole such that when the fastener is inserted in the through hole such that the outer surface contacts the inner surface the stabilization mechanism exerts a force on the fastener that resists relative movement of the fastener and the anchor body.

9. The fastener device of claim 8, wherein the stabilization mechanism includes a biasing member configured to expand as the head of the fastener contacts the biasing member, such that the expanded biasing member exerts the force on the outer surface of the fastener.

10. The fastener device of claim 9, wherein the anchor body defines a recess configured to receive the biasing member such that the biasing member is captured within the recess.

11. A fastener device configured to secure a spinal rod relative to a bone, the fastener device comprising:
an anchor body including an anchor body housing, the anchor body defining a through hole that extends through the anchor body housing, the anchor body further defining a rod-receiving channel that is configured to receive the spinal rod, the anchor body further including an upper end, a lower end, and an inner surface that defines a least a portion of the through hole, at least a portion of the inner surface defining a portion of a first sphere; and
a fastener including a head, a threaded shaft that extends out with respect to the head in a distal direction, and a neck that extends between the head and the threaded shaft, the head including an outer surface, at least a portion of the outer surface defining a portion of a second sphere, and the head further including a concave surface of the fastener that extends along both the head and the neck
wherein the fastener device defines a configuration in which both: 1) the portion of the outer surface rides along the portion of the inner surface, and 2) the anchor body abuts the neck at a location that is spaced in the distal direction from an entirety of the concave surface while the anchor body remains spaced from the entirety of the concave surface, such that movement of the fastener relative to the anchor body in at least one direction is blocked.

12. The fastener device of claim 11, wherein:
the fastener is elongate along a central axis that is parallel to the distal direction;
the portion of the outer surface includes a first point that is located in the distal direction with respect to all other points of the portion of the outer surface;
the concave surface includes a second point that is located in a proximal direction, which is opposite the distal direction, with respect to all other points of the concave surface; and
the first point is spaced from the central axis a first distance measured in a direction perpendicular to the distal direction, the second point is spaced from the central axis a second distance measured in a direction perpendicular to the distal direction, and the first distance is greater than the second distance.

13. The fastener device of claim 11, wherein the fastener is elongate along a central fastener axis that is parallel to the distal direction, the second sphere defines a first diameter, the neck defines a second diameter that is measured in a plane that is both normal to the central fastener axis and intersects the location, and the fastener defines a ratio of the first diameter to the second diameter in a range between about 2 to 1 and about 3 to 1.

14. The fastener device of claim 11, wherein the through hole extends away from the upper end and toward the lower end in a longitudinal direction, and the portion of the inner surface is closer to the lower end as measured along the longitudinal direction, than the portion of the inner surface is to the upper end as measured along the longitudinal direction.

15. The fastener device of claim 14, wherein the lower end defines a lower opening where the through hole exits the anchor body housing, the location is a first location, the anchor body defines a plane that includes an entirety of the lower opening, the head of the fastener defines a second location such that the fastener is devoid of any locations positioned in a proximal direction, which is opposite the distal direction, from the second location, and when the fastener device is in the configuration the second location is positioned a first distance from the upper end, the lower end is positioned a second distance from the upper end, the first distance and the second distance each measured along the longitudinal direction, and the first distance is greater than the second distance.

16. The fastener device of claim 14, wherein the second sphere defines a first diameter, the location is a first location, the inner surface defines a minimum inner diameter that is both: 1) measured at a second location that is on the inner surface, and 2) measured in a direction perpendicular to the longitudinal direction, and the first diameter is larger than the minimum inner diameter.

17. The fastener device of claim 16, wherein the upper end defines an upper opening where the through hole exits the anchor body housing, the upper opening defines an inner diameter measured in the direction perpendicular to the longitudinal direction, and the inner diameter is greater than both the first diameter and the second diameter.

18. The fastener device of claim 11, wherein the fastener is elongate along a central fastener axis that is parallel to the distal direction, the through hole extends away from the upper end and toward the lower end in a longitudinal direction along a central hole axis, and when the fastener device is in the configuration the central fastener axis is angularly offset from the central hole axis by an angle that is greater than 45 degrees.

19. The fastener device of claim 11, wherein all lines that: 1) lie entirely within a plane parallel to the distal direction, and 2) are tangent to the portion of the outer surface are noncollinear with all lines that: 1) lie entirely within the plane, and 2) are tangent to the concave surface.

20. The fastener device of claim 11, further comprising a stabilization mechanism configured to be positioned in the through hole such that when the fastener is inserted in the through hole such that the outer surface contacts the inner surface the stabilization mechanism exerts a force on the fastener that resists relative movement of the fastener and the anchor body.

21. The fastener device of claim 20, wherein the stabilization mechanism includes a biasing member configured to expand as the head of the fastener contacts the biasing member, such that the expanded biasing member exerts the force on the outer surface of the fastener.

22. The fastener device of claim 21, wherein the anchor body defines a recess configured to receive the biasing member such that the biasing member is captured within the recess.

23. A fastener device configured to secure a spinal rod relative to a bone, the fastener device comprising:
an anchor body including an anchor body housing and a central axis, the anchor body defining a through hole that extends through the anchor body housing along the central axis, the anchor body further defining a rod-receiving channel that is configured to receive the spinal rod, the anchor body further including an upper end, a lower end spaced from the upper end in a first direction, and an inner surface that defines at least a portion of the through hole, the inner surface including: 1) a first portion that defines a portion of a sphere having a first diameter, 2) a second portion that is cylindrical and that defines a second diameter that is equal to or greater than the first diameter, and 3) a third portion that defines a third diameter that is greater than both the first diameter and the second diameter, wherein the first portion terminates at the third portion in a direction that is opposite the first direction, and the third portion is disposed between the first portion and the second portion with respect to the first direction; and a fastener including a head and a threaded shaft that extends out with respect to the head, the head including an outer surface configured to articulate along the first portion of the inner surface when the fastener head is inserted in the through hole, wherein the sphere is a first sphere, the threaded shaft extends out with respect to the head in a distal direction, the fastener includes a neck that extends between the head and the threaded shaft, at least a portion of the outer surface is convex and defines a portion of a second sphere, the second sphere defining a first fastener diameter, the fastener includes a concave surface that extends along both the head and the neck, the neck defines a second fastener diameter measured: 1) in a direction perpendicular to the distal direction, and 2) at a location spaced in the distal direction of an entirety of the concave surface, and the fastener defines a ratio of the first fastener diameter to the second fastener diameter in a range between about 2 to 1 and about 3 to 1.

24. The fastener device of claim 23, further comprising a biasing member configured to be inserted into the through hole and positioned such that the biasing member is aligned with the third portion along a second direction that is perpendicular to the first direction.

25. The fastener device of claim 24, wherein the biasing member is a split ring that includes an inner surface that faces the central axis when the split ring is inserted in the through hole, the split ring defines a fourth diameter measured from a first point on the inner surface, through the central axis, to a second point on the inner surface in the second direction, and when the split ring is in an unbiased state the fourth diameter is less than each of the first diameter, the second diameter, and the third diameter.

26. The fastener device of claim 25, wherein the split ring includes an outer surface that faces away from the central axis when the split ring is inserted in the through hole, the split ring defines a fifth diameter measured from a first point on the outer surface, through the central axis, to a second point on the outer surface in the second direction, and when the split ring is in an unbiased state the fifth diameter is: 1) greater than the first diameter, 2) greater than the second diameter, 3) and less than the third diameter.

27. The fastener device of claim 23, wherein:

the fastener is elongate along a central axis that is parallel to the distal direction;

the portion of the outer surface includes a first point that is located in the distal direction with respect to all other points of the portion of the outer surface;

the concave surface includes a second point that is located in a proximal direction, which is opposite the distal direction, with respect to all other points of the concave surface; and the first point is spaced from the central axis a first distance measured in a direction perpendicular to the distal direction, the second point is spaced from the central axis a second distance measured in a direction perpendicular to the distal direction, and the first distance is greater than the second distance.

28. The fastener device of claim 27, wherein the location is a first location, the through hole extends away from the upper end and toward the lower end in a longitudinal direction, and the inner surface defines a minimum inner diameter that is both: 1) measured at a second location that is on the inner surface, and 2) measured in a direction perpendicular to the longitudinal direction, the second location is closer to the lower end as measured along the longitudinal direction, than the second location is to the upper end as measured along the longitudinal direction.

* * * * *